United States Patent
Chernyshov

(10) Patent No.: US 10,540,021 B2
(45) Date of Patent: Jan. 21, 2020

(54) DEVICE FOR DETERMINING THE POSITION OF AN OBJECT IN SPACE

(71) Applicant: OBSCHESTVO S OGRANICHENNOI OTVETSTVENNOSTYU "NASTEC", Khabarovsk (RU)

(72) Inventor: Evgeny Sergeevich Chernyshov, Khabarovsk (RU)

(73) Assignee: OBSCHESTVO S OGRANICHENNOI OTVETSTVENNOSTYU "NASTEC", Moscow (RU)

( * ) Notice: Subject to any disclaimer, the term of this patent is extended or adjusted under 35 U.S.C. 154(b) by 0 days.

(21) Appl. No.: 16/313,893

(22) PCT Filed: Jun. 22, 2017

(86) PCT No.: PCT/RU2017/050052
§ 371 (c)(1),
(2) Date: Dec. 28, 2018

(87) PCT Pub. No.: WO2018/017000
PCT Pub. Date: Jan. 25, 2018

(65) Prior Publication Data
US 2019/0171301 A1    Jun. 6, 2019

(30) Foreign Application Priority Data

Jul. 18, 2016 (RU) .................................. 2016129260

(51) Int. Cl.
G06F 3/0346 (2013.01)
G01C 21/08 (2006.01)
(Continued)

(52) U.S. Cl.
CPC ........... *G06F 3/0346* (2013.01); *G01C 21/08* (2013.01); *G01C 21/165* (2013.01); *G01C 21/18* (2013.01); *G01C 25/005* (2013.01)

(58) Field of Classification Search
None
See application file for complete search history.

(56) References Cited

U.S. PATENT DOCUMENTS

| 5,752,513 A | 5/1998 | Acker et al. | |
|---|---|---|---|
| 2013/0326364 A1* | 12/2013 | Latta | G06F 3/012 |
| | | | 715/751 |

FOREIGN PATENT DOCUMENTS

| DE | 19858147 A1 | 12/1999 |
|---|---|---|
| RU | 2103664 C2 | 3/2008 |
| RU | 2542793 C1 | 2/2015 |

\* cited by examiner

*Primary Examiner* — Nicholas J Lee
(74) *Attorney, Agent, or Firm* — Dmitry S. Kryndushkin, IP Center Skolkovo

(57) ABSTRACT

This invention relates to a measurement equipment and can be used to create means of measuring coordinates and angular values of an object freely moving in space with six degrees of freedom. The invention can be applied in human-machine interfaces as a coordinate input device, particularly, in training systems, in robotics, in augmented, virtual reality and mixed reality systems. The technical result is to increase the measurement accuracy by eliminating the measurement error of the gravity vector direction caused by the movement of the platform with sensors. There is the claimed device, wherein it comprises an inductance coil placed stationary in a horizontal plane, a power supply of the inductance coil, a computing unit, and a platform with sensors placed on a moving object, including a three-component magnetometer, three-component accelerometer and three-component gyroscope, with the power supply of the inductance coil includ- (Continued)

ing a coil current regulator controlled by a clock generator, and the computing unit is arranged with phase-locked loop, ensuring clocking of the magnetometer and synchronization of the magnetometer measurement phase with the phase of magnetic field pulses generated by the inductance coil.

9 Claims, 3 Drawing Sheets

(51) Int. Cl.
*G01C 21/16* (2006.01)
*G01C 21/18* (2006.01)
*G01C 25/00* (2006.01)

DEVICE FOR DETERMINING THE POSITION OF AN OBJECT IN SPACE

FIELD OF THE INVENTION

This invention relates to a measurement equipment and can be used to create means of measuring coordinates and angular values of an object freely moving in space with six degrees of freedom. The invention can be applied in human-machine interfaces as a coordinate input device, particularly, in training systems, in robotics, in augmented, virtual reality and mixed reality systems, and also in the gaining industry (as manipulators, game controllers, etc.), production sector (systems of positioning industrial equipment working parts, process control), CAD design (input systems, design process control).

BACKGROUND OF THE INVENTION

There is known a device for positioning object in space (patent RU2542793, Chernyshov E. S., G01C21/08, publ. 27 Feb. 2015). This invention on the essential features set is the closest to the claimed one and adopted for the prototype. The known device consists of an inductance coil (field source), a controlled current regulator, a digital three-component magnetometer, a digital three-component accelerometer and a computing unit. The known device determines the position of the object by measuring the gravity vector by the accelerometer and measuring the induction vector of the Earth's magnetic field and the magnetic field induction vector of the inductance coil located stationary in the horizontal plane by the magnetometer.

The disadvantages of the prototype can be attributed to low dynamic accuracy due to the presence of measurement errors by the accelerometer of the gravity vector direction caused by the presence of its own acceleration at the platform with sensors as it moves. In addition, the presence of the communication line between the computing unit and the current stabilizer negatively affects the ergonomic design of the device, and may limit the freedom of movement of the object.

SUMMARY OF THE INVENTION

The object of the invention is to create a simple by design, easy to use device for determining the position and orientation of a moving object that differs from the prototype by increased dynamic measurement accuracy, increased ergonomics and enhanced functionality (extensibility and modularity).

The technical result is to increase the measurement accuracy by eliminating the measurement error of the gravity vector direction caused by the movement of the platform with sensors.

The elimination of the error in measuring the gravity vector direction is achieved by the fact that the mobile platform with sensors is additionally equipped with a three-component gyroscope, the measurements of which are then used to correct the accelerometer measurements.

An additional effect achieved with the claimed invention is the elimination of the requirement for a communication line between the computing unit and the power supply.

The elimination of the requirement of a communication line between the computing unit and the power supply is achieved by the fact that the power supply additionally equipped with a clock generator, which using a given frequency supplies the controlled coil current regulator with a current reversal signal, and the computing unit is additionally equipped with a phase-locked loop unit for the magnetometer clocking and ensuring synchronization of the magnetometer measurement phase with the phase of the magnetic field pulses generated by the inductance coil.

The claimed device comprises an inductance coil placed stationary in a horizontal plane, a power supply for the inductance coil, a computing unit, and a platform with sensors placed on the moving object, said platform comprises a three-component magnetometer, a three-component accelerometer and a three-component gyroscope, wherein the power supply for the inductance coil comprises a coil current regulator controlled by a clock generator, and the computing unit is configured to provide a phase-locked loop, ensuring clocking of the magnetometer and synchronization of the magnetometer measurement phase with the phase of magnetic field pulses generated by the inductance coil.

In a particular embodiment, the computing unit of the claimed device may include a magnetic field frequency components selection unit, a unit for providing a phase-locked loop for magnetometer measurements, a unit for calculating orientation angles of the platform with sensors, a rotation compensation unit for the platform with sensors, a unit for calculating coordinates of the platform with sensors.

In another particular embodiment, the output of the clock generator is connected to the input of a current regulator, the outputs of which are connected to the terminals of the inductance coil.

In another particular embodiment, the output of the magnetometer is connected to the input of the magnetic field frequency components selection unit.

In another particular embodiment, the first output of the magnetic field frequency components selection unit is connected to the input of the phase-locked-loop frequency control unit, the second output is connected to the first input of the rotation compensation unit, the third output is connected to the orientation angle computing unit.

In another particular embodiment, the output of the phase-locked-loop frequency control unit is connected to the input of the magnetometer.

In another particular embodiment, the output of the gyroscope is connected to the second input of the orientation angle computing unit.

In another particular embodiment, the output of the accelerometer is connected to the third input of the orientation angle computing unit.

In another particular embodiment, the output of the orientation angle computing unit is connected to the second input of the rotation compensation unit, the output of which is connected to the input of the coordinate computing unit.

DETAILED DESCRIPTION OF THE INVENTION

Figure 1:
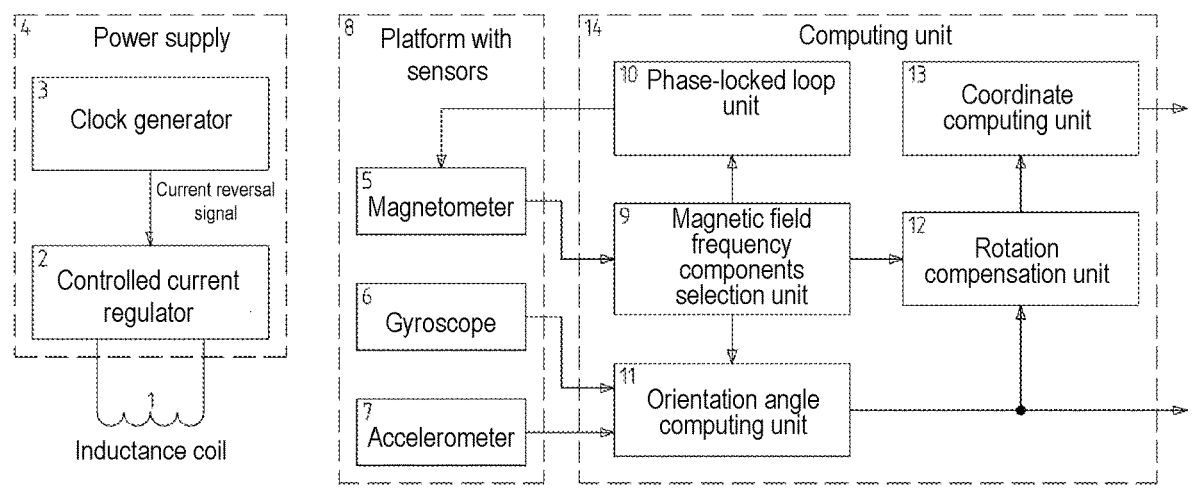
FIG. 1—The device schematic structure.

The claimed device consists of inductance coil 1 (field source) placed stationary in a horizontal plane and connected to controlled current regulator 2, which receives a signal to change the current polarity from clock generator 3 with a given frequency. Controlled current regulator 2 together with clock generator 3 form the power supply of inductance coil 4.

Digital three-component magnetometer 5, gyroscope 6 and accelerometer 7 are located on platform 8. Platform with sensors 8 is rigidly fixed to the moving object. Magnetometer 5, gyroscope 6 and accelerometer 7 interact with computing unit 14, which contains: magnetic field frequency components selection unit 9; phase-locked loop unit 10; orientation angle computing unit of the platform with sensors 11; rotation compensation unit of the platform with sensors 12; coordinate computing unit of the platform with sensors 13. Wherein the output of magnetometer 5 is connected to the input of magnetic field frequency components selection unit 9, the first output of which is connected to the input of phase-locked loop unit 10, the second output is connected to the first input of rotation compensation unit 12, the third output is connected to orientation angle computing unit 11, the output phase-locked loop unit 10 is connected to the input of magnetometer 5, the output of gyroscope 6 is connected to the second input of orientation angle computing unit 11, the output of accelerometer 7 is connected to the third input of orientation angle computing unit 11, output of orientation angle computing unit 11 is connected to the second input of rotation compensation unit 12, the output of which is connected to the input of coordinate computing unit 13.

Inductance coil 1 can be made by winding an insulated wire onto a cylindrical base, or it can be made in the form of a planar coil manufactured with concentric turns of a conductor on a printed circuit board, or in another method. Wherein it is undesirable to use a ferromagnetic core, since this will lead to significant local distortions of the Earth's magnetic field. However, this is permissible if the coil is small and the sensor is sufficiently removed from the coil during device operation.

The diameter of inductance coil 1, the number of turns and the conductor section are determined on the basis of the problem to be solved, to ensure the necessary radius of the device working area, power consumption and weight and size of the coil. In the general case, an increase in the diameter and number of turns, without a proportional reduction in the coil current, will lead to an increase of the working area, simultaneously with a decrease in weight and size and an increase in power consumption caused by a proportional increase of the coil active resistance. It is necessary to increase the conductor section to reduce energy consumption, which will also reduce the weight and size, and may significantly affect the prime cost of the coil.

The working area means the area of space around inductance coil 1, in which the positioning of platform with sensors 8 is performed. The size of the working area depends on the characteristics of inductance coil 1, power supply 4 and magnetometer 5, as well as on the required measurement accuracy. In the first approximation, the measurement error is proportional to the square of the distance from the magnetometer to the inductance coil [1], therefore, it is necessary to limit the size of the working area of the device to ensure the required measurement accuracy. Wherein outside the working area, the accuracy of measurements at one or several coordinates will be lower than the required value. A further increase in the distance leads to a decrease in the induction value of the magnetic field, measured by the magnetometer, below the magnetometer sensitivity/error level, which makes it impossible to determine the coordinates of the platform with sensors.

The time constant of inductance coil 1 is also an important characteristic, since it determines the duration of the coil current polarity switch, which, in turn, affects the maximum achievable measurement frequency of the device. It is necessary to reduce the time constant, i.e. reduce inductance and/or increase the active electrical resistance of the coil to reduce the duration of polarity switch.

The control part of current regulator 2 and clock generator 3 can be assembled on discrete electronic components according to known schemes, or implemented using a microcontroller. In the second case, the clock generator will represent a subprogram of the microcontroller.

Magnetometer 5 can be represented by a three-component magnetic field induction sensor of any known type (magnetoresistive sensor, Hall effect sensor), made in the form of a chip with a digital output, using MEMS technology (microelectromechanical systems), or in the form of an assembly that includes three orthogonal sensitive elements, as well as an amplification and analog-to-digital signal conversion circuit. A prerequisite is that the magnetometer has a single measurement mode with an external signal to start the measurement. Suitable models of magnetometers are STMicroelectronics LIS3MDL, MEMSIC MMC3416xPJ, and similar ones.

Gyroscope 6 and accelerometer 7 represent three-component sensors, made according to the MEMS technology, in the form of a chip with a digital output.

In prime cost and mass and size terms, the most preferable option is to use a combined sensor made in the form of a single digital MEMS chip, including a three-component magnetometer, a three-component gyroscope and a three-component accelerometer. Such a sensor, for example, is STMicroelectronics LSM9DS1.

Platform with sensors 8 represent a printed circuit board on which magnetometer 5, gyroscope 6 and accelerometer 7 are located. If using digital sensors made by MEMS technology, platform 8 can have dimensions less than 15×15×3 mm.

Computing unit 14 can be represented by a microcontroller or personal/single-board computer, while internal units 9, 10, 11, 12, 13 of the computing unit represent subprograms. the computing unit implements an algorithm for determining the coordinates of an object based on information about the value of the artificial magnetic field vector at a given point in space, together with an algorithm for determining the orientation of an object.

There are various methods of organizing the device power. The power unit of the calculating unit (not indicated in FIG. 1) can be placed both in the same enclosure with the computing unit and separately from it. If the computing unit is represented by a personal computer, then, as a rule, it includes a power unit with the required characteristics. the computing unit can also power the sensors.

The claimed device operates as follows.

Figure 2:
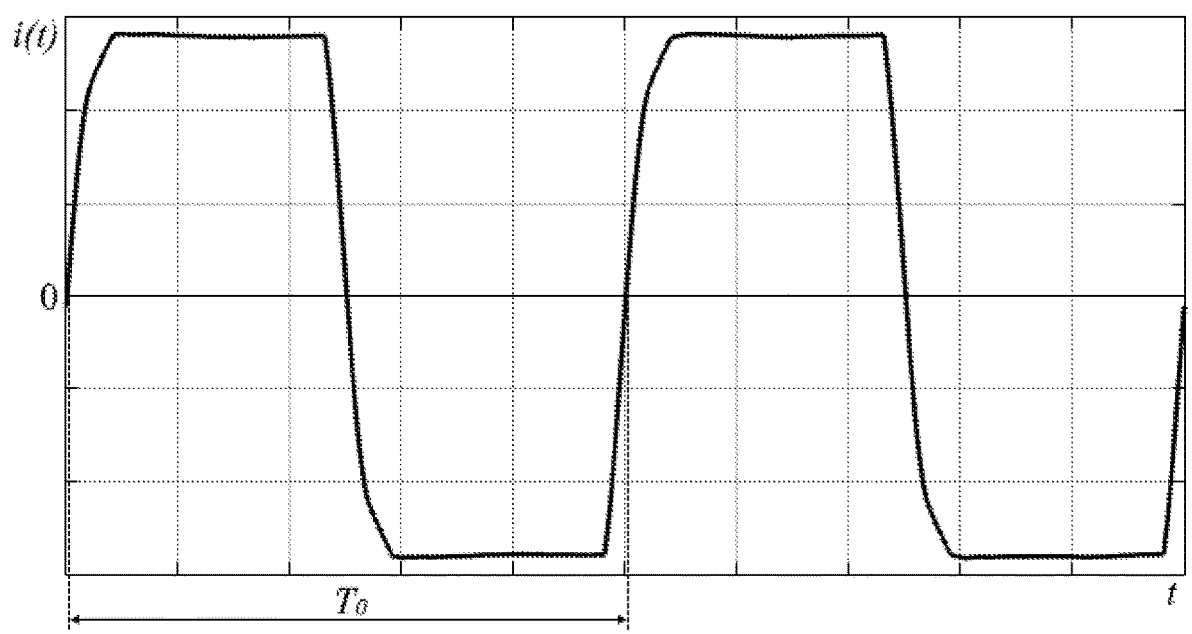
FIG. 2—The graph of the inductance coil current versus time.

Controlled current regulator 2 supplies coil 1 with a current signal i(t) of alternately positive and negative polarity (FIG. 2). The polarity of the signal i(t) is determined by the periodic control signal generated by clock generator 3. The current passing through coil 1 creates a magnetic field. The artificial magnetic field of coil 1 is added to the Earth's magnetic field and magnetometer 5 measures the magnetic induction vector of the total field. Wherein gyroscope 6 measures the angular velocity of the platform with sensors, accelerometer 7 measures the gravity vector acting on the platform with sensors.

The maximum measurement frequency $f_{mag}$ of magnetometer 5 must satisfy the following condition for correct operation of magnetic field frequency components selection unit 9 and phase-locked loop unit 10:

$$f_{mag} \geq \frac{4}{T_0},$$

where $T_0$ is the signal period of inductance coil 1 (see FIG. 2).

The measurement frequencies of gyroscope 6 and accelerometer 7 are not standardized, and can be any, suitable for solving the problem. For example, for efficient digitalization of human movements, a measurement frequency of 200 Hz is sufficient.

The readings of sensors 5, 6 and 7 in digital form are transmitted to computing unit 14.

It is assumed for simplicity that the coordinate systems of sensors 5, 6 and 7 coincide with the coordinate system associated with mobile platform 8. Otherwise, the readings of the sensors should be presented in computing unit 14 to a single is coordinate system associated with the mobile platform.

Computing unit performs the following operations to determine the coordinates and orientation of platform with sensors 8.

Magnetic field frequency components selection unit 9 produces an accumulation of measurements on each axis of magnetometer 5 for an integer of inductance coil 1 signal periods (at least one period), and then selects a constant component of the magnetic field—the induction vector of the Earth's magnetic field $\vec{B}_E$, and also the variable component of the magnetic field—the magnetic field induction vector of the inductance coil $\vec{B}_S$. The Fourier transform, in which the Walsh functions [2] serve as the basis, is used for this purpose. Other transformation methods may be used.

As a result of the transformation, we obtain the amplitude and phase values of each of the three components of the magnetic field variable component, corresponding to the three axes of magnetometer 5 measurements.

In this case, the component phase characterizes its sign as follows: if the phases of the two measured components coincide, then the components have the same sign; if the phases differ by $\pi$ (half period), then the components have opposite signs; a phase jump of $\pi$ corresponds to a change in the sign of the component. Thus, the vector $\vec{B}_S$ can have two opposite directions. Unambiguous determination the direction of the vector $\vec{B}_S$ is hampered by phase ambiguity associated with the uncertain location and orientation of the sensor in space.

Phase ambiguity can be removed in several ways.

In particular, a coarse priori information about the initial position and orientation of the object can be known (located in a given sector of coordinates, has a given orientation). In such a case, the phase ambiguity can be removed immediately after the start of measurements. Then phase-locked loop unit 10 will track the signal phase as long as platform with sensors 8 is in the magnetic field of inductance coil 1.

Another option is to use a specific time pattern in the signal of inductance coil 1, which allows an unambiguous determination of the measured signal phase. The simplest pattern can be, for example, a different duration of the positive and negative signal pulses.

The phase value of each of the three components of the magnetic field variable component is then transmitted to phase-locked loop unit 10, in which the algorithm for minimizing the error between the specified and measured signal phase is performed by adjusting the frequency of the magnetometer measurements (for example, the PID control algorithm).

The magnetometer should be started in the single measurements mode with an external signal of the measurement start, in which case the computing unit will be able to change its measurement frequency flexibly by changing the signal generation period for the measurement start.

As a result of the unit 10 operation, the frequency and phase of the magnetometer 5 measurements will correspond to the frequency and phase of the inductance coil 1 signal.

At the next stage of calculations, the induction vector value of the Earth's magnetic field $\vec{B}_E$ is transferred from unit 9 to orientation angle computing unit 11, which also receive measurements of gyroscope 6 and accelerometer 7.

Measurements of accelerometer 7 represent the gravity vector. Due to the low accuracy characteristics of the sensors used, as well as due to the influence of various disturbances (pickups from electrical equipment, vibration and accelerated movement of the platform with sensors), the values $\vec{B}_E$ and $\vec{G}$ can be very noisy. Therefore, to improve measurement accuracy, without reducing the dynamic characteristics of the device, it is necessary to use measurements of gyroscope 6 for complementary filtering of the vectors $\vec{B}_E$ and $\vec{G}$ direction.

We use rotation matrices [3] to rotate vectors at angles obtained by integrating gyroscope measurements. Let the measurement period of the gyroscope and the measurement period of the vectors $\vec{B}_E$ and $\vec{G}$ be equal to $T_0$. Then the recursive complementary filter [4] will have the following form:

$$\vec{B}_{Ef} = (1-\delta) R_x(W_x T_0) R_y(W_y T_0) R_z(W_z T_0) \vec{B}_{Ef} + \delta \vec{B}_E;$$

$$\vec{G}_f = (1-\delta) R_x(W_x T_0) R_y(W_y T_0) R_z(W_z T_0) \vec{G}_f + \delta \vec{G},$$

where $\vec{B}_{Ef}$—the filtered induction vector of the Earth's magnetic field; $\delta$—filter coefficient, $\delta \ll 1$; $W_x$, $W_y$, $W_z$—the measured gyroscope rotation speeds around the x, y, z axes, respectively; $T_0$—the measurement period of the gyroscope; $R_x(W_x T_0)$—matrix of rotation about the x axis through an angle of $W_x T_0$; $R_y(W_y T_0)$—matrix of rotation about they axis through an angle of $W_y T_0$; $R_z(W_z T_0)$—matrix of rotation about the z axis through an angle of $W_z T_0$; $G_f$—filtered gravity vector.

The orientation angles are calculated in a known manner [3], in the direction of the vectors $\vec{B}_{Ef}$ and $\vec{G}_f$.

Next, the obtained orientation angles of the object are used in rotation compensation unit 12, for converting the magnetic field induction vector of inductance coil $\vec{B}_S$ from the coordinate system of magnetometer 5 to the coordinate system associated with fixed inductance coil 1. The vector $\vec{B}_S$ is rotated for this purpose by the angles opposite to the obtained angles of the object orientation. The vector rotation is performed by using the rotation matrices:

$$\vec{B}_{S0} = R_z(-\psi) R_y(-\theta) R_x(-\phi) \vec{B}_S,$$

where $\vec{B}_{S0}$—the magnetic field induction vector of the inductance coil in the coordinate system associated with inductance coil 1 (at $\phi=\theta=\psi=0$); $\phi$, $\theta$, $\psi$—obtained angles of object orientation (angles of bank, pitch, and yaw, respectively); $R_z(-\psi)$—matrix of rotation about the z axis through an angle of $-\psi$; $R_y(-\theta)$—matrix of rotation about the y axis through an angle of $-\theta$; $R_x(-\phi)$—matrix of rotation about the x axis through an angle of $-\phi$.

The vector $\vec{B}_{S0}$ is then transmitted to coordinate computing unit 13. Let the vector $\vec{B}_{S0}$ have the following form:

$$\vec{B}_{S0} = \begin{bmatrix} B_{S0x} \\ B_{S0y} \\ B_{S0z} \end{bmatrix}.$$

Since inductance coil 1 is located horizontally, the azimuthal angle of the vector $\vec{B}_{S0}$ direction in the spherical coordinate system (the angle between the vector projection on the x0y plane and the x axis of the inductance coil 1 coordinate system) coincides with the azimuthal coordinate $\varphi$ of the object being positioned:

$$\varphi = \mathrm{atan2}\left(\frac{B_{S0y}}{B_{S0x}}\right).$$

The remaining coordinates (radius vector and zenith angle) of the object can be obtained analytically [1], or using a table-specific function [3]. In the second case, the table represents an array of points of the vertical plane passing through the vertical z axis of the inductance coil 1 coordinate system (the coil axis of symmetry). Each point is associated with a magnetic induction vector generated by an inductance coil at that point. Calculation of vectors can be made using the Biot-Savart law. It is necessary to find the magnetic induction vectors in the table closest in magnitude and direction to the vector $\vec{B}_{S0}$, and their coordinate values to determine the coordinates of an object. Then you can determine the desired object coordinates, for example, using bilinear interpolation [5].

Figure 3:
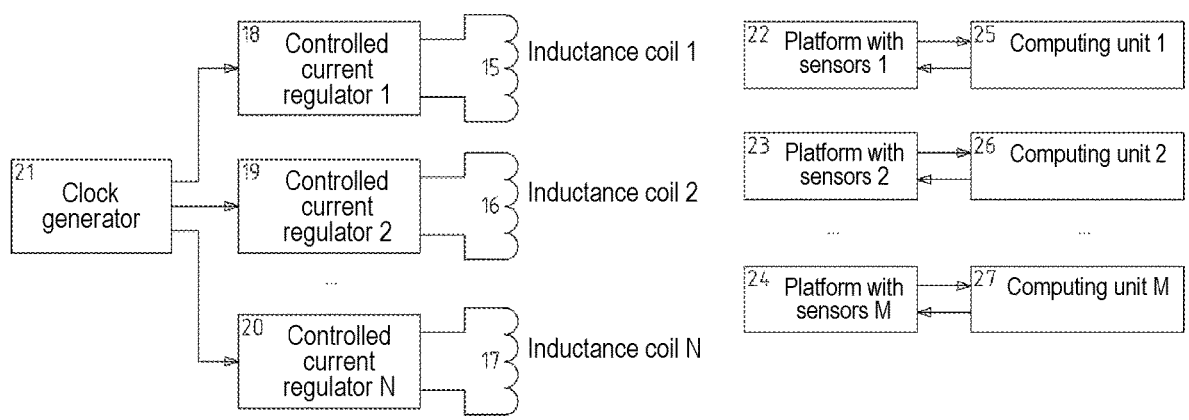
FIG. 3—Topology of a system containing several field sources and several independent positioned objects.

The described structure and principle of operation of the device allows flexible increasing in the number of positioned objects and expansion of the device working area. FIG. 3 shows an option of the system topology, which includes several field sources and several independent platforms with sensors.

The state of the art of computer technology allows the use of a separate miniature Computing unit (pos. 25, 26, 27) for each platform with sensors (pos. 22, 23, 24). This approach, together with the lack of a communication line between the computing units and the power supply of the inductance coil, allows the number of positionable objects to be increased indefinitely without making any changes to the construction of the device.

Several inductance coils (pos. 15, 16, 17) can be used, located separately, to expand the working area of the device. In this case, the coil signals should have a frequency or time separation, in order to prevent their mixing at the boundary between the working areas of several coils. The selection of a signal of a particular coil can be carried out using a Fourier transformation with a basis in the form of Walsh functions [2], or in other ways.

An indefinite phase difference between the signals of neighboring inductance coils may lead to the device's phase-locked-loop frequency control unit unsynchronization when an object is moved from the working area of one inductance coil to the working area of another inductance coil. The signals of the coil power supplies must be synchronized with each other to eliminate this problem.

The most suitable way to achieve this goal is to connect the inputs of the controlled coil current regulators (pos. 18, 19, 20) to the outputs of one common clock generator 21, which provides the signals generation of the required frequency and phase.

In the general case, alternation of field sources with at least four different frequencies (at frequency division) or phases (at time division) of a signal is required [6] to create a working area of arbitrary size and shape. However, if the presence of "dead" zones is acceptable, then alternation of field sources with two or three different frequencies/phases is also possible.

DESIGNATIONS USED IN THE DRAWINGS pos. 1—Inductance coil;
pos. 2—Controlled current regulator;
pos. 3—Clock generator;
pos. 4—Power supply
pos. 5—Magnetometer;
pos. 6—Gyroscope;
pos. 7—Accelerometer;
pos. 8—Platform with sensors;
pos. 9—Magnetic field frequency components selection unit;
pos. 10—Phase-locked loop unit;
pos. 11—Orientation angle computing unit;
pos. 12—Rotation compensation unit;
pos. 13—Coordinate computing unit;
pos. 14—Computing unit;
pos. 15—Inductance coil 1;
pos. 16—Inductance coil 2;
pos. 17—Inductance coil N;
pos. 18—Controlled current regulator 1;
pos. 19—Controlled current regulator 2;
pos. 20—Controlled current regulator N;
pos. 21—Clock generator;
pos. 22—Platform with sensors 1;
pos. 23—Platform with sensors 2;
pos. 24—Platform with sensors M;
pos. 25—Computing unit 1;
pos. 26—Computing unit 2;
pos. 27—Computing unit M.

DATA SOURCES

1. Raab F., Blood E., Steiner O., Jones H. Magnetic position and orientation tracking system//IEEE Transactions on Aerospace and Electronics Systems.—Vol. AES-15, No. 5, September 1979.—P. 709-717.
2. Zalmanzon L. A. Fourier, Walsh, Haar transforms and their application in control, communication and other fields.—M.: Science. Ch. ed. phys.-mat. lit., 1989.-496 p.
3. Chye E. U., Chernyshov E. S. Magnetic inertial method for determining the position and orientation of an object// Bulletin of Pacific National University.—2014.—No. 1 (32).—p. 69-78.
4. Chernyshov E. S., Otchesky S. A. Microelectromechanical systems for tracking movements//Current issues in scientific work and educational activities: a collection of scientific papers on the materials of the International Scientific and Practical Conference on Jan. 31, 2013: in 13 parts. Part 8.—Tambov: Publishing house of Tambov Regional Public Organization Business-Science-21:) Society, 2013.—P. 147-148

5. Yaroslaysky L. P. Introduction to digital image processing.—M.: Sov. radio, 1979.—312 p.

6. Zhelamskii M. V. Features of the construction of a positioning field for local navigation in enclosed spaces// Measurement Techniques.—2014.—No. 7.—p. 40-45; Zhelamskii M. V. Features of the construction of a positioning field for local navigation in enclosed spaces// Measurement Techniques.—2014.—Vol. 57.—No. 7. P. 791-799.

The invention claimed is:

1. A device for positioning an object in space, comprising an inductance coil placed stationary in a horizontal plane, a power supply for the inductance coil, a computing unit, and a platform with sensors placed on the moving object, said platform comprises a three-component magnetometer, a three-component accelerometer and a three-component gyroscope, wherein the power supply for the inductance coil comprises a coil current regulator controlled by a clock generator, and the computing unit is configured to provide a phase-locked loop, ensuring clocking of the magnetometer and synchronization of the magnetometer measurement phase with the phase of magnetic field pulses generated by the inductance coil.

2. The device according to claim 1, wherein the computing unit comprises a magnetic field frequency components selection unit, a unit for providing a phase-locked loop for magnetometer measurements, a unit for calculating orientation angles of the platform with sensors, a rotation compensation unit for the platform with sensors, a unit for calculating coordinates of the platform with sensors.

3. The device according to claim 1, wherein the output of the clock generator is connected to the input of the current regulator and outputs of the current regulator are connected to the terminals of the inductance coil.

4. The device according to claim 2, wherein the output of the magnetometer is connected to the input of the magnetic field frequency components selection unit.

5. The device according to claim 4, wherein the first output of the magnetic field frequency components selection unit is connected to the input of the unit for providing a phase-locked loop, the second output is connected to the first input of the rotation compensation unit, the third output is connected to the unit for calculating orientation angles.

6. The device according to claim 4, wherein the output of the unit for providing a phase-locked loop is connected to the input of the magnetometer.

7. The device according to claim 2, wherein the output of the gyroscope is connected to the second input of the unit for calculating orientation angles.

8. The device according to claim 2, wherein the output of the accelerometer is connected to the third input of the unit for calculating orientation angles.

9. The device according to claim 2, wherein the output of the unit for calculating orientation angles is connected to the second input of the rotation compensation unit, the output of which is connected to the input of the unit for calculating coordinates.

* * * * *